(12) United States Patent
Park et al.

(10) Patent No.: US 10,537,327 B2
(45) Date of Patent: Jan. 21, 2020

(54) MINIMALLY INVASIVE SURGERY TISSUE (MIST) CLIP

(71) Applicants: Adrian Edward Park, Crownsville, MD (US); Charles Francis Knapp, Georgetown, KY (US)

(72) Inventors: Adrian Edward Park, Crownsville, MD (US); Charles Francis Knapp, Georgetown, KY (US)

( * ) Notice: Subject to any disclaimer, the term of this patent is extended or adjusted under 35 U.S.C. 154(b) by 333 days.

(21) Appl. No.: 14/675,157

(22) Filed: Mar. 31, 2015

(65) Prior Publication Data
US 2015/0272585 A1    Oct. 1, 2015

Related U.S. Application Data (60) Provisional application No. 61/967,981, filed on Mar. 31, 2014.

(51) Int. Cl.
*A61B 17/22*    (2006.01)
*A61B 17/08*    (2006.01)

(52) U.S. Cl.
CPC .................................. *A61B 17/083* (2013.01)

(58) Field of Classification Search
CPC ... A61B 17/083; A61B 17/122; A61B 17/068; A61B 17/1285
See application file for complete search history.

(56) References Cited

U.S. PATENT DOCUMENTS

| | | | | |
|---|---|---|---|---|
| 3,598,125 A * | 8/1971 | Cogley | ............... | A61B 17/1227 24/507 |
| 3,601,127 A * | 8/1971 | Finegold | ................ | A61B 17/08 24/542 |
| 3,802,437 A * | 4/1974 | Kees, Jr. | ............ | A61B 17/1227 24/510 |
| 3,827,438 A * | 8/1974 | Kees, Jr. | ............ | A61B 17/1227 24/545 |
| 4,217,902 A * | 8/1980 | March | .................. | A61B 17/083 606/157 |
| 4,416,266 A * | 11/1983 | Baucom | ............. | A61B 17/1227 24/560 |
| 4,484,581 A * | 11/1984 | Martin | ............... | A61B 17/1227 606/158 |
| 4,556,060 A * | 12/1985 | Perlin | ................ | A61B 17/1227 24/552 |
| 4,616,651 A * | 10/1986 | Golden | ................ | A61B 17/128 606/142 |
| 4,638,804 A * | 1/1987 | Jewusiak | ............. | A61B 17/122 606/158 |
| 4,777,949 A | 10/1988 | Perlin | | |

(Continued)

FOREIGN PATENT DOCUMENTS

WO    02/096303    12/2002

OTHER PUBLICATIONS

International Search Report dated Sep. 1, 2015, issued in International Application No. PCT/US2015/023647.

(Continued)

*Primary Examiner* — Julie A Szpira (74) *Attorney, Agent, or Firm* — Steptoe & Johnson LLP (57) ABSTRACT

Clips, or clasps for temporarily attaching lines and devices during refraction or for compressing, ligating or dissecting various vessels and ducts are often required during surgical (e.g., arteries, veins and the common bile duct) and non-surgical procedures.

28 Claims, 6 Drawing Sheets

(56) References Cited

U.S. PATENT DOCUMENTS

| | | | | |
|---|---|---|---|---|
| 4,791,707 A | * | 12/1988 | Tucker | A61B 17/083 227/120 |
| D331,462 S | * | 12/1992 | Kraus | D24/143 |
| 5,207,692 A | * | 5/1993 | Kraus | A61B 17/083 227/901 |
| 5,236,440 A | * | 8/1993 | Hlavacek | A61B 17/0644 227/902 |
| 5,695,505 A | * | 12/1997 | Yoon | A61B 17/0487 606/151 |
| 5,779,720 A | * | 7/1998 | Walder-Utz | A61B 17/083 606/142 |
| 7,896,895 B2 | * | 3/2011 | Boudreaux | A61B 17/064 606/157 |
| 8,246,639 B2 | * | 8/2012 | Kassab | A61B 17/122 606/151 |
| 9,572,579 B2 | * | 2/2017 | Weisshaupt | A61B 17/1227 |
| 9,931,124 B2 | * | 4/2018 | Gokharu | A61B 17/1285 |
| 2005/0251183 A1 | * | 11/2005 | Buckman | A61B 17/08 606/157 |
| 2006/0100646 A1 | * | 5/2006 | Hart | A61B 17/083 606/151 |
| 2006/0195125 A1 | * | 8/2006 | Sakakine | A61B 17/083 606/157 |
| 2008/0004637 A1 | * | 1/2008 | Klassen | A61B 17/122 606/142 |
| 2008/0132915 A1 | * | 6/2008 | Buckman | A61B 17/08 606/138 |
| 2013/0245653 A1 | * | 9/2013 | Litherland | A61B 17/128 606/158 |
| 2015/0057684 A1 | * | 2/2015 | Zieris | A61B 17/1227 606/151 |
| 2015/0164510 A1 | * | 6/2015 | Pleil | A61B 17/1227 606/157 |
| 2016/0038149 A1 | * | 2/2016 | Ladjali | A61B 17/00234 606/142 |

OTHER PUBLICATIONS

Written Opinion of the International Searching Authority dated Sep. 1, 2015, issued in International Application No. PCT/US2015/023647.

Notification Concerning Transmittal of International Preliminary Report on Patentability (Chapter I of the Patent Cooperation Treaty) dated Oct. 13, 2016, issued in International Application No. PCT/US2015/023647.

* cited by examiner

MINIMALLY INVASIVE SURGERY TISSUE (MIST) CLIP

CLAIM OF PRIORITY

This application claims the benefit of prior U.S. Provisional Application No. 61/967,981 filed on Mar. 31, 2014, which is incorporated by reference in its entirety.

TECHNICAL FIELD

The invention relates to a clip device for use during surgical or non-surgical procedures.

BACKGROUND

A variety of surgical procedures can require the temporary attachment of strings, wires, nets or devices using clips, to tissue flaps, organs, or organ flaps during retraction, for example. In other procedures, clips may be required to compress, ligate or dissect arteries and veins and ducts such as the common bile duct.

An important factor in the appropriate attachment of these devices is the practicality of the clips that grip tissue and other materials or compress vessels and ducts. For example, to clear a field of view or work area, a segment of the liver may need to be held back in order to perform surgery on a segment of the intestine. This process can be demanding and typically can require an extra person to hold a conventional retractor. This procedure is even more challenging during minimally invasive surgery (MIS) where a trocar port and surgical technician may be devoted primarily to holding tissue back from the field of view or work area. Likewise demanding in MIS are procedures, for example, to ligate or dissect arteries and veins and the common bile ducts. Any clip used in these types of procedures must pass through a trocar and must be easily grasped and opened and closed by typically long shafted MIS graspers in order to be practical. The clip devices described herein meets these requirements.

SUMMARY

Clips, or clasps for temporarily attaching lines and devices during refraction or for temporarily compressing, ligating or dissecting various vessels, tubes and ducts are often required during surgical (e.g. arteries, veins and the common bile duct) and non-surgical procedures. In one embodiment, the standard Minimally Invasive Surgery Tissue (MIST) clip (herein referred to as the clip) in its simplest form is constructed from a single wall sleeve that allows for the jaws of commercially available surgical graspers to slide inside so that the clip becomes an extension of the grasper. Opening the jaws of the grasper opens the clip; closing the jaws of the grasper closes the clip. When the clip is closed with tissue between its atraumatic jaws, the elastic properties of the clip anchors the clip in place and allows for the grasper to be removed. Release of the gripping force and removal of the clip is accomplished by reinserting the surgical grasper and opening the grasper's jaws.

In another embodiment of the present invention, the standard clip, in a more elaborate form, is constructed of several sleeves that allows for the jaws of commercially available surgical graspers to slide inside so that the clip becomes an extension of the grasper. Opening the jaws of the grasper opens the clip; closing the jaws of the grasper ratchets down the clip thereby gripping any material between the clip's jaws. The grasper can be removed leaving the clip gripping the tissue of interest. Release of the gripping force and removal of the clip is accomplished by reinserting the grasper and opening the grasper's jaws which engages the release mechanism.

The compactness of the clip device can make it suitable for surgery, especially minimally invasive surgery (MIS). For example, clips can be attached to make up the two ends of a line refractor. One clip on the end of the line retractor can be used to move tissue from a work space. Another clip on the other end of a line retractor can be attached to non-movable tissue or suture loop. With both clips gripping the appropriate material and with the cessation of pulling on the line retractor, tension will remain in the line refractor thereby keeping the tissue in place and away from the work area. Release of the clips by the graspers will allow for removal of the line refractor. Multiple clips, for example, could be used as part of a net retractor for the distribution of force loads over delicate organs or tissue masses during retraction.

In one aspect, the more elaborate standard clip includes a circular shaped double-walled-sleeve with two attached jaws (referred to as the primary sleeve) for clamping on to various materials; a vertical slot in the back and two small slots in the front of the primary sleeve through which the jaws of a commercially available grasper or forceps can slide; two additional very small holes in the primary sleeve through which a ratcheting pin can protrude; an inner circular shaped sleeve (affixed at one end only to the primary sleeve) with a cut out in the back and groves or holes constituting part of the ratcheting mechanism track on each side; and an outer partial circular sleeve (affixed at one end only to the primary sleeve) that contains the ratcheting pin and makes up part of the release mechanism.

In another aspect, the primary sleeve is constructed from a flexible material such that when forces are applied by external graspers to open its jaws, the clip's circular shape will easily elongate vertically to produce a "C" shape, thereby open its jaws as well.

In another aspect, when the clip is being opened a release mechanism is engaged by the upward force of the grasper jaws allowing the free end of the inner sleeves to slide freely in the channel of the primary sleeve, thereby allowing the clip to open freely.

In another aspect, when the clip is being closed, a ratcheting pin on the outer sleeve, which protrudes through a small opening in the primary sleeve, rides on the ratcheting track of the inner sleeve in such a way that the clip will maintain the compressive force on the tissue after the external grasper is removed.

In another aspect, the simpler standard clip includes a primary sleeve constructed from a single sheet (as opposed to double wall), with no ratcheting mechanism, and with sufficient stiffness in the material to hold a compressive force on the tissue when closed.

In another aspect, the jaws of the clip can have atraumatic grooved surfaces to minimize tissue damage.

In another embodiment, the clip can have a "house slipper" shape (slipper clip) which allows for its application to be the same as that described for the simple and elaborate standard clip.

In another aspect, the slipper clip is composed of two flat plates, hinged at the back, with atraumatic jaws at the front and semicircular or similar shaped sleeves permanently attached to the outside top and bottom of the two flat plates. The sleeves are aligned so that grasper jaws can pass through. Small vertical plates act as "stops" and limit the depth of penetration of the grasper during application.

In the simplest embodiment, the simple slipper clip has semicircular sleeves that can be single walled. The gripping force of the clip's jaws can be provided by the elastic properties of the hinge and/or elastic bands placed over the two semicircular sleeves.

In the more elaborate embodiment, the elaborate slipper clip can have double wall sleeves with curved (rectangular shaped) channels inside to guide thin flexible ratcheting tracks that make up part of the ratcheting mechanism and connect and control, in part, the opening and closing positions of the top and bottom hinged flat plate/jaws.

In another aspect, one end of each ratcheting track is permanently fixed to the inside track of the bottom sleeve and the other end is free.

In another aspect, a small flexible wire (release mechanism) is located inside the upper sleeve, passing through two holes in the inside surface of the sleeve and communicating with the holes or slanted grooves in the ratcheting tracks. When grasper ends are expanded, one of the ends will slightly deform the wire upward thereby releasing the wire ends from the holes or slanted grooves in the ratcheting track and releasing the gripping force of the elaborate slipper clip.

In various embodiments, one or more of the following features can be employed. The material of the clips can be made from various plastics or metals, including super elastic shape memory metals, or combinations of both plastics and metals. The ratcheting track of the inner sleeve can be a series of holes of various shapes, or slanted groves. The pin of the ratcheting mechanism can be made of a spring material such that it will slide over the track (producing a clicking sound) and yet sufficiently strong to stay in place and prevent the clips' jaws from opening when the tissue between the jaws opposes the compressive forces as the jaws are closed.

In another aspect, clips can be sized and attached to various devices, for example a line refractor, for deployment through a trocar. In this situation, with two clips as part of the refractor, one end of the line can be anchored to an organ and the other end to a suture loop through the abdominal wall using a conventional MIS grasper.

Additional objects, advantages and other novel features of the invention will be set forth in part in the description that follows and in part will become apparent to those skilled in the art upon examination of the foregoing or may be learned with the practice of the invention.

BRIEF DESCRIPTION OF THE DRAWINGS

FIG. 3 is a drawing (not to scale) depicting a double wall primary sleeve of an elaborate standard clip with a line for attachment to various devices such as line retractor and the like.

DETAILED DESCRIPTION

The Minimally Invasive Surgery Tissue (MIST) clip described herein allows for the jaws of most commercially available tools, such as surgical graspers, to slide inside so that the clip becomes an extension of the grasper. Opening the jaws of the grasper opens the clip; closing the jaws of the grasper closes the clip thereby gripping any material between the clip's jaws. In one embodiment, the gripping forces are produced by the elastic properties of the clip and in another, by a ratcheting mechanism. The surgical grasper can be removed leaving the clip gripping the material of interest. Release of the gripping force and removal of the clip is accomplished by reinserting, opening, and then closing the surgical grasper. Lines, wires, loops or various devices can be attached to the clip or it can be free of lines, wires and the like (i.e., a free standing clip). The compactness of the clip can make it suitable for surgery, especially minimally invasive surgery (MIS).

A clip can be easily engaged, anchored, and removed using commercially available tools.

In one embodiment, a clip can include a primary sleeve with atraumatic jaws. The shape of the clip can be any kind of closed shape, for example, circular, semi-circular, triangular, rectangular, square, pentagonal, octagonal, or of similar shape and have a slit on one side. There can be a cut out opposite to atraumatic jaws for insertion of a tool to open and close the atraumatic jaws. There can be two holes in the front of the sleeve for the tips of a tool to be inserted. There can be a plate located on the top and bottom of the jaws (and in front of each of the two holes in the primary sleeve) to limit the insertion depth of the grasper's tips.

The clip can be constructed of a semi-flexible material that allows for the sleeve to be expanded from a closed shape to an open shape. The semi-flexible material can have recoil properties that allow the primary sleeve to return to its closed shape after deformation to an open shape. The semi-flexible material can be plastic, spring steel and shape memory metal, with recoil properties that provide a gripping force to anchor the clip to the tissue.

The outer edges of the sleeve can be reinforced with material to insure desired clip expansion and recoil properties.

In another embodiment, a clip can include a primary sleeve with atraumatic jaws, an inner sleeve with holes or grooves for ratcheting, and an outer sleeve with pins for holding and releasing the gripping action of the clip. The clip can have a double walled primary sleeve with atraumatic jaws. The shape of the clip can be any kind of closed shape, for example, circular, triangular, rectangular, square, or of similar shape and have a slit on one side. There can be a cut out opposite to atraumatic jaws for insertion of a tool to open and close the atraumatic jaws. There can be two holes in the front of the sleeve for the ends of the tool to be inserted. There can be a plate located on the top and bottom of the jaws (and in front of each of the two holes in the primary sleeve) to limit the insertion depth of the grasper's tips.

In certain embodiment, there can be two holes in the top of the primary sleeve will line up with the holes in or grooves on the track of the inner sleeve and with the protruding pin on the outer sleeve.

In certain embodiment, there can be an inner sleeve with similar shape as that of the primary sleeve (minus the jaws). The inner sleeve can have a similar cut out as in the primary sleeve, but with one end of the inner sleeve cut away (called the free end) leaving two tracks on each side of the sleeve. Each track can have a row of holes or slanted grooves in the center of the track or teeth on the track edge on which an angled flexible pin can slide over in one direction but lock in place in the opposite direction. The inner sleeve can be located in-between the double walls ("channels") of the primary sleeve. The end of the inner sleeve can be permanently attached to the bottom of the primary sleeve. The row of holes or grooves in the two tracks of the inner sleeve can line up with the two small holes in the front of the primary sleeve. The hole in the non-free end of the inner sleeve can be lined up with a hole in the primary sleeve through which a tool end passes.

In certain embodiment, an outer semi-flexible sleeve can fit over the primary sleeve. Two semi-flexible pins can be affixed to the outer sleeve and positioned at the front of the sleeve with spacing so as to align with the center of each track of the inner sleeve. In certain embodiment, one end of the outer sleeve is permanently fixed to the bottom of the primary sleeve. The free end of the outer sleeve is located partially over the opening of one of the holes in the primary sleeve through which a tool ends pass. The free end of the outer sleeve can be positioned such that it can be lifted up from the surface of the primary sleeve when the jaws of the tool are opened. The pins affixed to the free end of the outer sleeve can be disengaged from the tracks of the inner sleeve when the outer sleeve is lifted.

The outer sleeve can have elastic properties such that the free end can return to the upper surface of the primary sleeve when the jaws of the tool are closed. The pins affixed to the free end of the outer sleeve can engage the row of holes or grooves in the tracks of the inner sleeve when the jaws of the grasper are closed.

The clip can have a single wall sleeve and two independent ratcheting tracks.

A method of using a clip can include inserting a tool into the clip, opening a sleeve or sleeves (if there are multiple sleeves including an inner sleeve and/or an outer sleeve) from a closed shape to an open shape, clipping a tissue in-between the jaws, and retracting the tool so that the tissue is remained clipped in-between the jaws. In certain embodiment, when the clip opens, the inner sleeve (with only one end attached to the primary sleeve and the other end free) can expand to an open shape such that the surfaces of the two sleeves will slide in opposite directions to each other. When the clip opens, the pins affixed to the outer sleeve will be disengaged from the track thereby releasing the ratcheting mechanism and freeing the gripping force of the clip jaws. The angled pins affixed to the outer sleeve can slide over the hole or groves in the track of the inner track (ratcheting mechanism) when the clip is closing with tissue between the jaws and resist forces by the compressed tissue to open. Closure of the clip by a tool allows the grasper operator to "ratchet down" the desired gripping force of the clip's jaws, thereby transferring the gripping force of the grasper handles to the jaws of the clip.

Various devices can be attached by a string or wire loosely looped around the back of the clip, or tied through small holes in the back of the sleeves of the clip. In certain embodiment, the clip can fit through a surgical trocar.

In certain embodiment, a tool that has been inserted into the clip and opened, thereby opening the clip, then ratcheting closed with tissue between the jaws of the clip to anchor a line or device and finally removed to clear the work space. In certain embodiment, a tool, that has been inserted into a clip already anchored in tissue, can be 1) opened, thereby raising the ratcheting pin and allowing the jaws of the clip to open, and 2) removed through a trocar, for example, with the clip attached.

In certain other embodiment, a clip can include two flat plates, hinged at the opposite side of atraumatic jaws. In certain embodiment, two closed shaped (e.g. semicircular or similar shaped) sleeves can be attached to the outside top and bottom of the two flat plates and aligned so that a tool can pass through. In certain embodiment, small vertical plates, attached to the top and bottom of the outer surfaces of the two flat plates in front of the semicircular sleeves, act as "stops" and limit the depth of penetration of the grasper during application.

The tissue gripping force of the clip can be provided by the elastic properties of the hinge at one end of the two flat plates and/or elastic bands placed over the two semicircular sleeves. The semicircular (or similar shaped) sleeves can be double walled with a curved (rectangular shaped) channel inside to guide thin semi-flexible ratcheting tracks. The semi-flexible tracks can have holes or slanted grooves and can be two-dimensional circular shaped arcs segments. The tracks can be sufficiently flexible to bend in three dimensions as they ride in the channels of the semicircular sleeves. One end of each track can be permanently fixed to the inside track of the bottom sleeve and the other end is free.

In certain embodiment, a small flexible wire can be located inside the upper sleeve, passing through two holes in the inside surface of the sleeve and communicating with the holes or slanted grooves in the ratcheting tracks. A method of using this clip can include inserting a tool into the clip and expanding so that a tool end can slightly deform the wire upward thereby releasing the wire ends from the holes or slanted grooves in the ratcheting track. When the tool closes, the grasper ends move away from the wire and the wire ends engage in the tracks producing the desired ratcheting movement and desired holding force when the grasper is removed.

In certain embodiment, a clip is free standing (i.e. without lines, wire or loops in the back) and the atraumatic jaws are sufficiently elongated so they can be used for anchoring to tissue (e.g. to support retractors) and/or to temporarily occlude lumens (e.g. of blood vessels for hemostasis or bile duct/bowel to avoid spillage, etc.), for compression, ligation or dissection of various vessels (such as arteries and veins) and ducts (such as the common bile duct) and/or for marking anatomical locations such as during laparoscopic surgery.

Figure 2A:
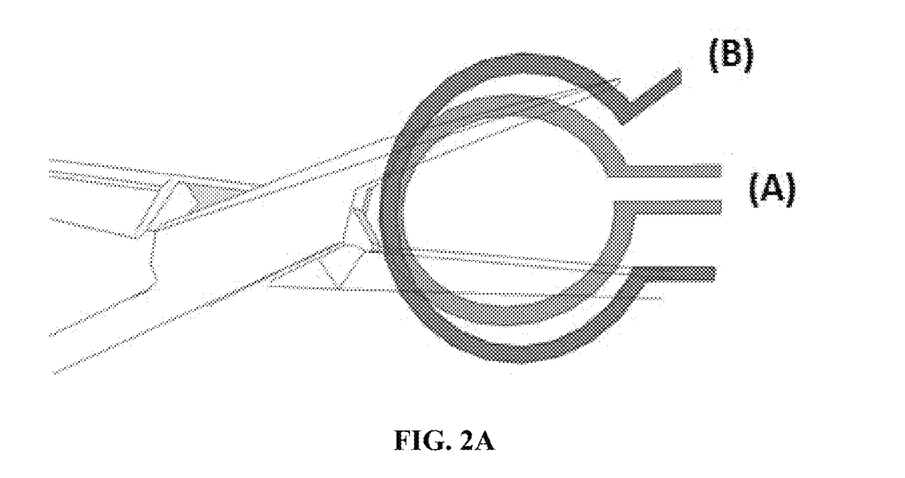
FIG. 2A is a side view sketch depicting how upward forces, produced by the opening jaws of a grasper or forceps, open the clip from a closed state (A) to an opened state (B).
Figure 2B:
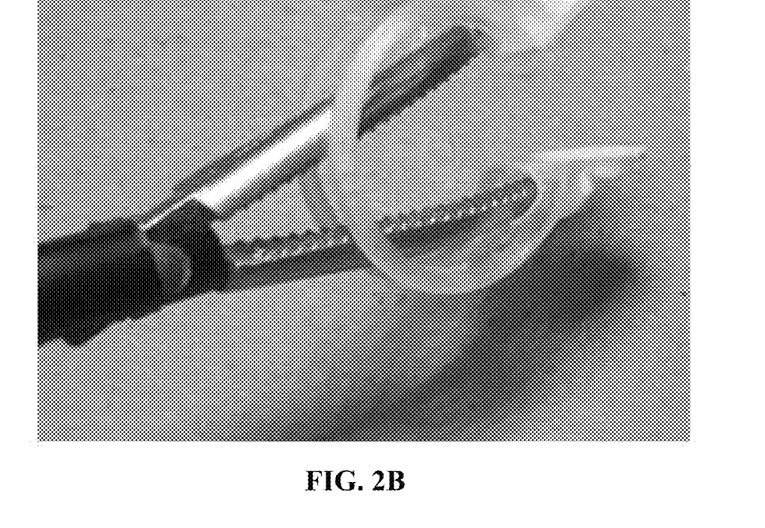
FIG. 2B is a side view of the simple standard clip showing grasper jaws engaged and opened.

Clips for temporarily attaching lines or devices are often required during retraction or the securing of items during any surgical or non-surgical procedure. The MIST clip (the clip) allows for the jaws of a tool, such as surgical grasper, to slide inside so that it becomes an extension of the grasper (FIG. 2B). Opening the jaws of the grasper opens the clip; closing the jaws of the grasper closes (ratchets down) the clip thereby gripping any material between the clip's jaws. The surgical grasper can be removed leaving the clip gripping the material of interest. Release of the gripping force and removal of the clip is accomplished by reinserting the surgical grasper and opening the grasper's jaws thereby engaging the release mechanism. The flexibility and compactness of the clip device makes it suitable for surgery, especially minimally invasive surgery (MIS), but can be used wherever any attachment clip is required.

Figure 1:
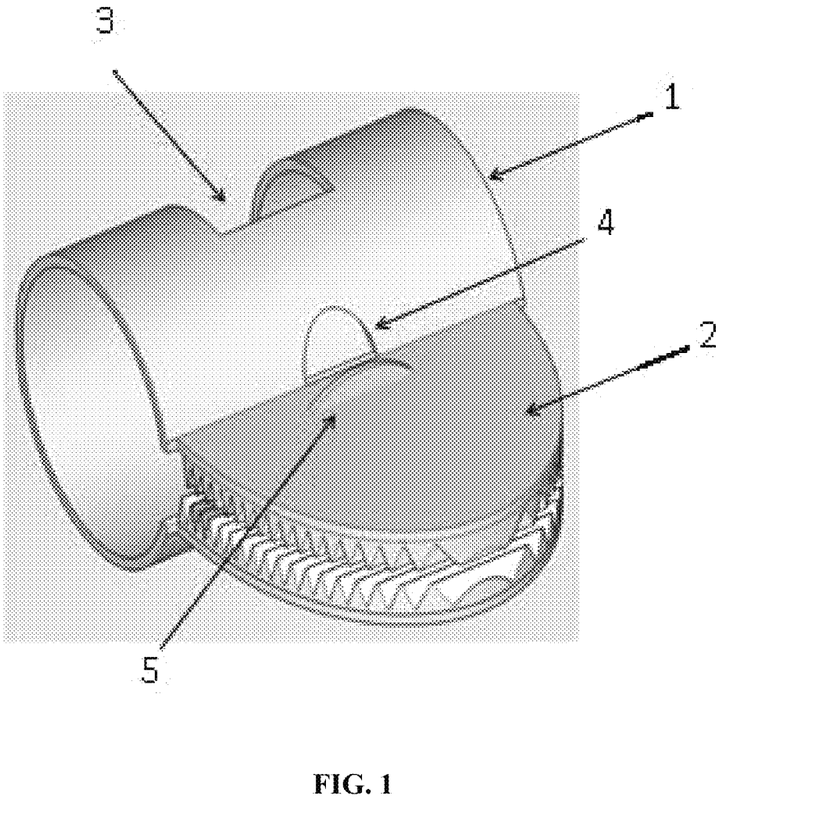
FIG. 1 is a drawing (not to scale) depicting a view of a single wall primary sleeve and attached atraumatic jaws of a simple standard clip.

In its simplest form (FIG. 1), the clip can be constructed of a primary semi-flexible circular or a similar-shape sleeve, with a slit on one side 1 to which is permanently attached two atraumatic jaws 2 with surfaces to hold tissue. The sleeve can have a large opening 3 on the opposite side of the jaws and two small semi-circular openings 4 in the sleeve near the top and bottom surfaces of the jaws 2 through which the jaws of a grasper can be inserted. "Stops" 5 are located in front of the semi-circular openings to limit insertion of a grasper to the appropriate depth. With the graspers inserted into the clip, opening of the jaws of the grasper can cause the primary sleeve to change from the circular shaped "closed state" (A) to a "C" shaped "opened state" (B), as shown in FIGS. 2A and 2B. The elastic properties of the sleeve will determine the gripping force of the clip's jaws. The clip can be constructed of semi-flexible material with recoil properties that allows the primary sleeve to maintain its circular shape after deformation to the "C" shape, such as plastic, spring steel and shape memory metal, with recoil properties that provide a gripping force to anchor the clip to the tissue.

Figure 3:
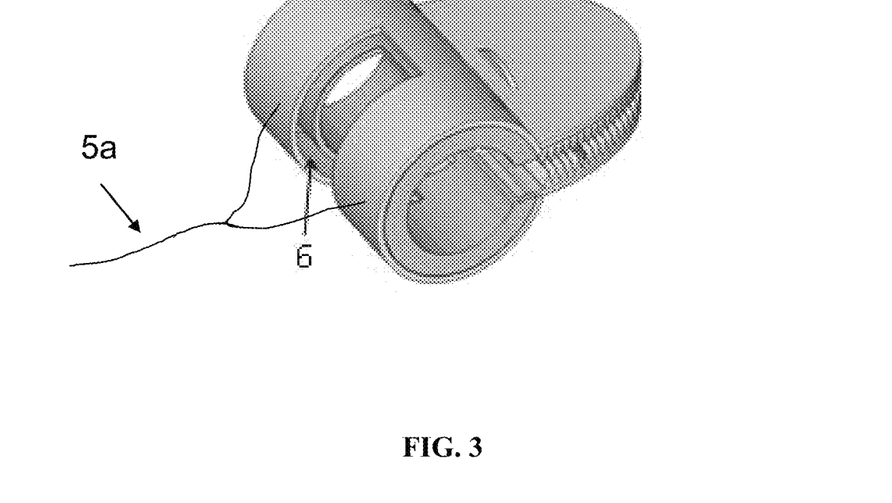

The clip can be attached to any device by a line 5a (FIG. 3) or wire looped through the back of the sleeve or through holes in the back of the sleeve. In this configuration, for example, two clips can be part of each end of an adjustable "line" retractor, passed through a trocar, and used to control the position of internal organs and the like during surgery. The clip can be made of inexpensive materials which would make it disposable for surgical applications. The clip can be made of materials that can be sterilized and capable of being prepackaged, sterile, in a suitable container.

Figure 4:
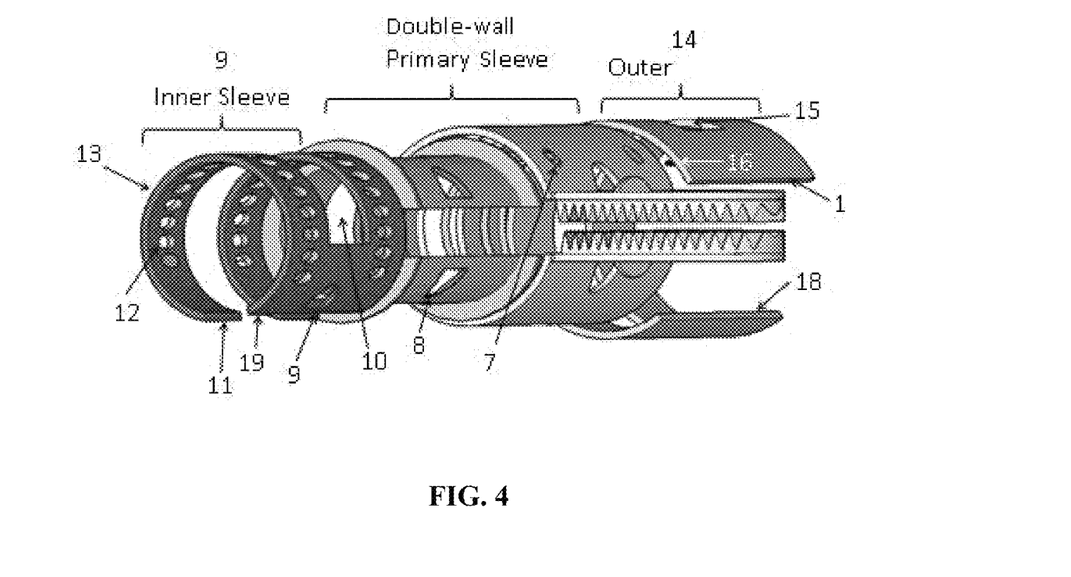
FIG. 4 is a drawing (not to scale) of an elaborate standard clip depicting an expanded view of the "double wall" primary sleeve (middle), the inner sleeve (far left) and the outer sleeve (far right), including the flexible ratcheting pin shown attached to the inside surface of the outer sleeve (upper right).
Figure 5A:
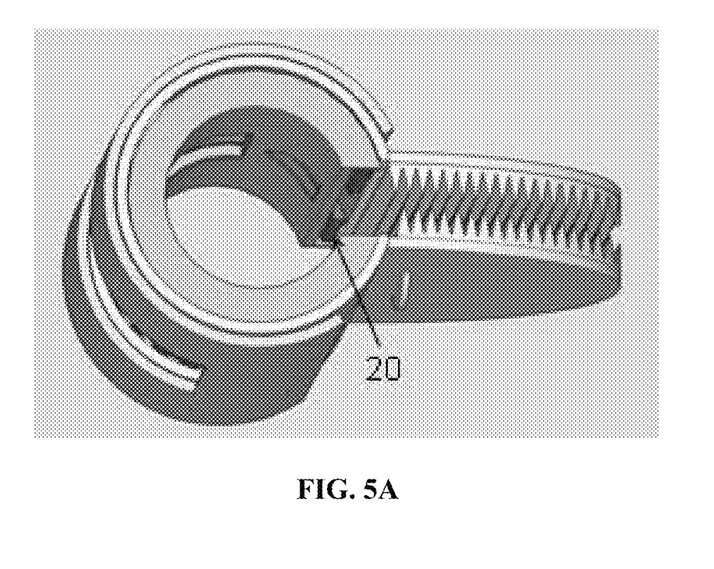
FIG. 5A is a drawing (not to scale) depicting a fully assembled elaborate standard clip, showing the ratcheting sleeve positioned (20) in the channel of the primary sleeve.
Figure 5B:
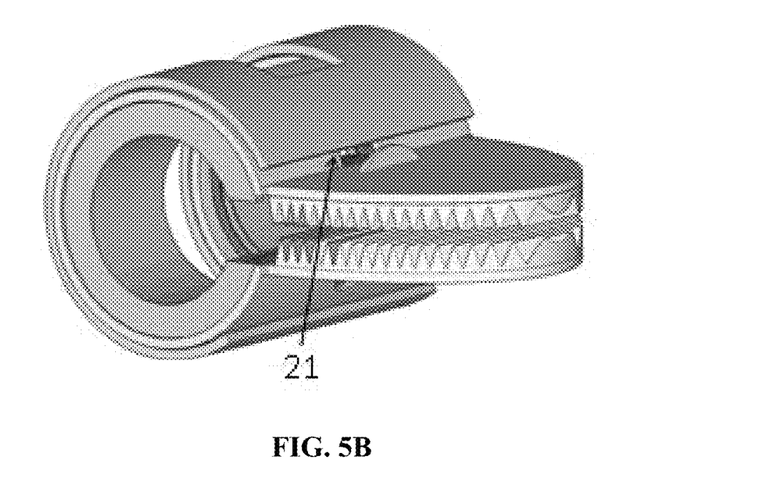
FIG. 5B is a drawing (not to scale) depicting a fully assembled elaborate standard clip, showing the position (21) of the edge of the outer sleeve relative to the opening for the jaw end of the graspers which serves as part of the release mechanism.

The clip can also be constructed so that the gripping forces on the tissue are not solely from the elastic properties of the primary sleeve. In this configuration, the clip, called the elaborate clip, can be composed of: 1) a primary semi-flexible, double wall, circular sleeve, with a slit on one side 6 to which are permanently attached atraumatic jaws with surfaces to hold tissue, 2) an inner sleeve 9 as part of the ratcheting mechanism to hold the clip's jaws in place to produce gripping forces on the tissue, and 3) an outer sleeve 14 with two semi-flexible pins 16 to complete the ratcheting/release mechanism. The primary sleeve can have a large opening in the back 3 and two small semi-circular openings 4 in the sleeve near the top and bottom surfaces of the jaws through which the jaws of a grasper can be inserted. "Stops" 5 can be located in front of the semi-circular openings to limit insertion of a grasper to the appropriate depth. Inside the channel 6 of the primary sleeve is located the inner sleeve 9 which has a similar cut out in the back as the primary sleeve, but with one end cut away, leaving two tracks 13 on each side of the sleeve. The tracks can have a row of holes 12 or slanted grooves down the center or slanted grooves along the track edge (facing the middle of the clip) on which an angled flexible pin can slide over in one direction but lock in place in the opposite direction. The inner sleeve is located in the channel 20 of the doubled wall primary sleeve. The end 19 of the inner sleeve that holds the two tracks can be permanently attached to the bottom of the primary sleeve.

With the graspers inserted into the clip, opening of the jaws of the grasper can cause the primary and inner sleeve to change from the circular shaped "closed state" (A) to a "C" shaped "opened state" (B), as shown in FIG. 2A. However, with one end of the inner sleeve attached to the primary sleeve and the other end free 11, the two sleeves will slide relative to each other. Two holes 7 are also located in the top surface of the primary sleeve such that they are aligned over the holes or slanted grooves on the two tracks of the inner sleeve. These holes in the top of the primary sleeve allow for two flexible, angled, pins 16 of the outer sleeve to pass through and slide over the inner track. The bottom end 18 of the outer sleeve can be permanently attached at the bottom of the primary sleeve so that the free end 17 is located 21 partially over the hole in the primary sleeve through which the end of the grasper jaws pass. With this arrangement, the free end of the outer sleeve can slightly separate from the surface of the primary sleeve when an upward force is applied by the jaws of graspers. The slight separation of the free end of the outer sleeve allows for the pins to disengage from the holes or grooves in the track; thereby releasing the gripping force on the tissue. Moving the clip from the opened position to the closed position with the grasper jaws will cause the pins 16 on the outer sleeve to ride over the holes or grooves in the track 13 (producing a licking sound). When the clip is closed to produce the appropriate compressive force on the tissue, the grasper can be removed and the pin will be engaged in the holes or grooves of the tracks, thereby not allowing the clip to open. Reinsertion of the grasper jaw into the clip followed by an expansion of the grasper jaws will lift the free end 17 of the outer sleeve and the attached pins 16, thereby opening the clip for removal from the tissue. This configuration allows for the surgeon to apply compressive forces on the tissue as desired. As in the simpler design, the elaborate clip can be attached to any device by a line 5a or wire looped through the back of the sleeve or through holes in the back of the sleeves. In this configuration, for example, two elaborate clips can be part of each end of an adjustable "line" retractor, passed through a trocar, and used to control the position of internal organs and the like during surgery. The scalable size of the elaborate clip makes it uniquely suitable for minimally invasive surgery. The elaborate clip can be made of relative inexpensive materials (such as plastics) which would minimize cost and make it disposable for surgical applications thereby reducing risk of complications including infection. Other materials could include spring stainless steel and shape memory metals. The elaborate clip can be made of materials that can be sterilized and capable of being prepackaged, sterile, in a suitable container. The clips can also be used for non-medical application where access to a site is limited and lines, wire or/or devices are to be anchored.

In another embodiment, the elaborate clip can have a slightly different way in which the ratcheting mechanism is fabricated. In this embodiment, the primary sleeve can be a single wall sleeve and the ratcheting tracks (with holes or slanted grooves), much like those in the elaborate clip, but where the tracks are not attached as shown in 9, i.e., there are two independent tracks. The tracks are permanently fixed at one end to the lower part of the primary sleeve and the other end is free. Three small bands are affixed on each side of the primary sleeve to ensure alignment of the track during opening and closing of the clip. An outer sleeve with an engage/release mechanism is affixed to the primary sleeve in a similar manner as that of the elaborate clip.

In another embodiment, the clip can have a "house slipper" shape (slipper clip) which allows for its application to be the same as that described for the simple and elaborate clip. The slipper clip (FIGS. 6 and 7) is composed of two flat plates 22, hinged at the back 30, with atraumatic jaws 31 at the front. Permanently attached to the outside top and bottom of the two flat plates are two semicircular or similar shaped sleeves 24 aligned so that grasper jaws can pass through. Small vertical plates 27, permanently attached to the top and bottom of the outer surfaces of the two flat plates and in front of the semicircular sleeves, act as "stops" and limit the depth of penetration of the grasper during application. In the simplest embodiment (simple slipper clip), the semicircular sleeves can be single walled. The holding force of the clip can be provided by the elastic properties of the hinge and/or elastic bands placed over the two semicircular sleeves. In this embodiment, no ratcheting mechanism is available, only the compressive forces offered by the elastic hinge and/or band are available for anchoring to tissue and the like.

Figure 6:
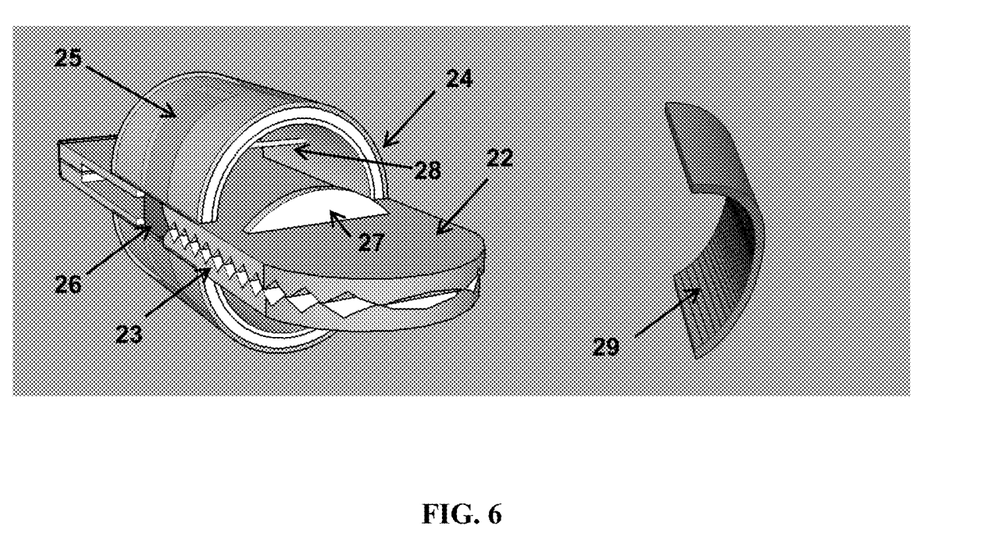
FIG. 6 is a drawing on the left (not to scale) depicting a fully assembled slipper clip, showing a double wall primary sleeve 24, a ratcheting track channel 25, a ratcheting track 26, grooves 29 (left drawing), and ratcheting release mechanism 28.
Figure 7:
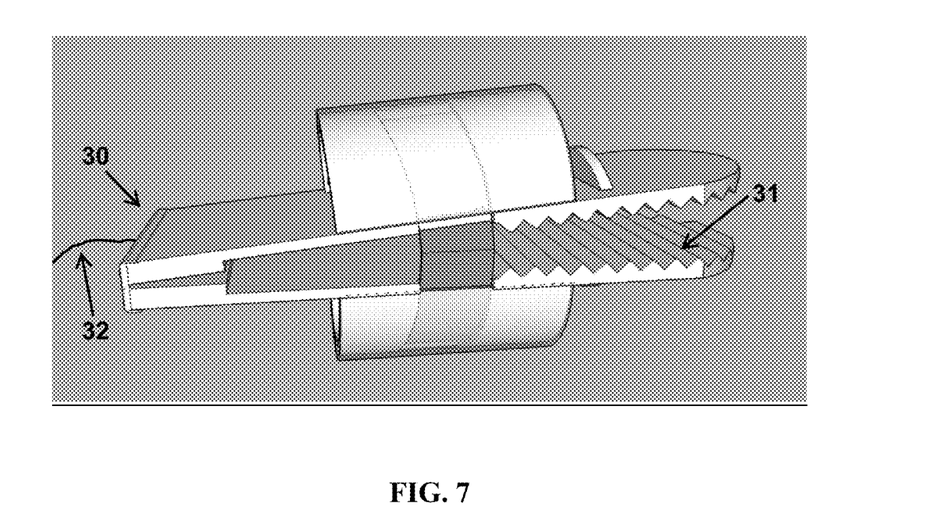
FIG. 7 is a drawing (not to scale) depicting a fully assembled slipper clip in the opened position showing the hinge 30, atraumatic jaws 31 and a line 32 for attachment to a device such as a line refractor.

In the elaborate slipper clip, the semicircular (or similar shape) sleeves are double walled 24 with a curved (rectangular shaped) channel 25 inside to guide thin flexible ratcheting tracks 26. The tracks, with holes or slanted grooves, are two dimensional circular shaped arc segments that make up part of the ratcheting mechanism and connect and control, in part, the opening and closing positions of the top and bottom hinged flat plate/jaws. The tracks are sufficiently flexible to bend in three dimensions as they ride in the channel 25 of the semicircular sleeves. One end of each track is permanently fixed to the inside track of the bottom sleeve and the other end is free. A very small flexible wire 28 is located inside the upper sleeve, passing through two holes in the inside surface of the sleeve and communicating with the holes or slanted grooves 29 in the ratcheting tracks. When the grasper ends are inserted into the elaborate slipper clip and expanded, one of the grasper ends will slightly deform the wire upward, thereby releasing the wire ends from the holes or slanted grooves in the ratcheting track. When the grasper closes, the grasper ends move away from the wire and the wire ends engage in the tracks and produce the desired ratcheting movement and desired holding force when the grasper is removed. In either configuration of the slipper clip, lines 32, wires or loops can be affixed to the back for attaching various devices such as a line retractor and the like.

Figure 8:
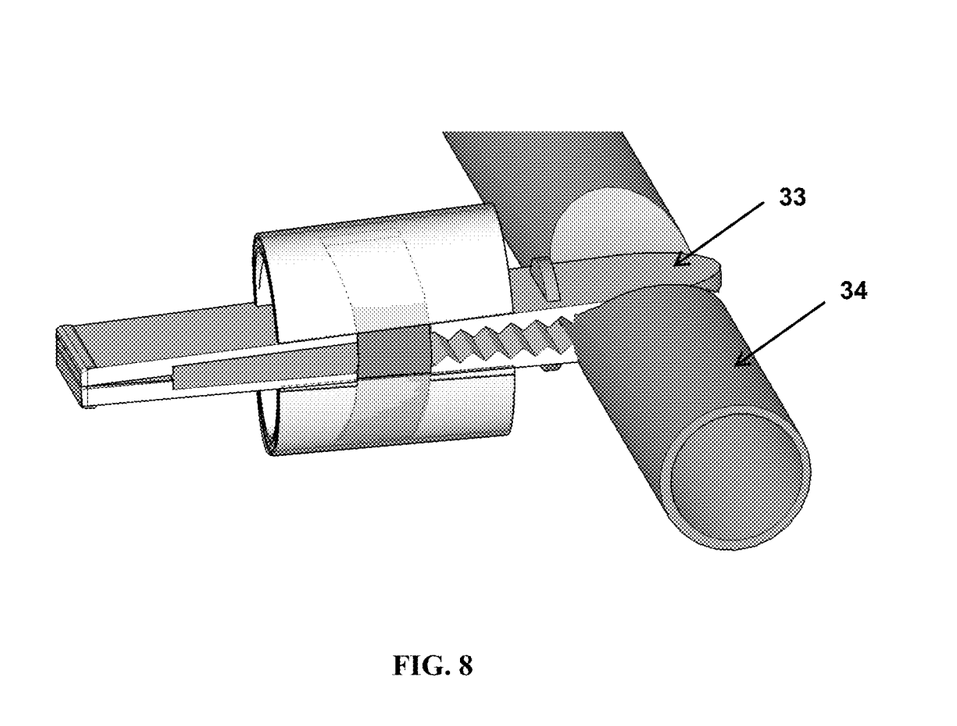
FIG. 8 is a drawing (not to scale) depicting a fully assembled free standing (i.e. without any lines, wire or loops attached at the back) slipper clip with thin elongated atraumatic jaws compressing a vessel.

In another embodiment, the clip can be free standing (i.e. without any lines, wire or loops attached at the back) (FIG. 8) and configured with narrow elongated atraumatic jaws 33 as opposed to the blunt shaped nose for holding tissue of the standard and slipper clip designs previously described. Otherwise, all aspects of the free standing clip would be the same as those of the standard and slipper clips. The free standing clips would have applications especially in Laparoscopy surgery where long handled graspers could be inserted into the clip and with its elongated atraumatic jaws used to compress, ligate or dissect various vessels 34 (such as arteries and veins) and ducts (such as the common bile duct). Free standing clips could also be used to mark anatomical locations during surgery. This embodiment could have applications in other surgical and non-surgical procedures.

Other embodiments are within the scope of the following claims.

What is claimed is:

1. A clip comprising:
a primary sleeve with jaws having atraumatic grooved surfaces,
an inner sleeve, and
an outer sleeve for holding the gripping action of the clip,
wherein the primary sleeve and inner sleeve include a cut out portion opposite to the jaws having atraumatic grooved surfaces for insertion of a grasper to open and close the jaws, such that when the jaws are in an open position, the clip is structured to receive the grasper and become an extension of the grasper, and when the jaws are in a closed position, the elastic properties of the clip anchors the clip in place and allows for the grasper to be removed.

2. The clip of claim 1, wherein the clip has a closed shape with a slit on one side.

3. The clip of claim 1, wherein the cut out portion includes two holes in the front of the sleeve for tips of a tool to be inserted.

4. The clip of claim 1, wherein the jaws include a top plate and a bottom plate that limit the insertion depth of the tips of the tool.

5. The clip of claim 3, wherein is the cut out portion includes a plate in front of the two holes in the primary sleeve.

6. The clip of claim 1, wherein the clip includes a semi-flexible material that allows for the sleeve to be expanded from a closed shape to an open shape.

7. The clip of claim 6, wherein the semi-flexible material has recoil properties that allow the primary sleeve to return to its closed shape after deformation to the open shape.

8. The clip of claim 7, wherein the semi-flexible material is selected from a group consisting of plastic, spring steel and shape memory metal.

9. The clip of claim 1, wherein the sleeve includes outer edge reinforcing materials configured to enhance the clip expansion and recoil properties.

10. A clip comprising:
a primary sleeve with jaws having atraumatic grooved surfaces,
an inner sleeve with holes or grooves for ratcheting; and
an outer sleeve with protruding pins for holding and releasing gripping action of the clip
wherein the primary sleeve and inner sleeve include a cut out portion opposite to the jaws having atraumatic grooved surfaces for insertion of a grasper to open and close the jaws, such that when the jaws are in an open position, the clip is structured to receive the grasper and become an extension of the grasper, and when the jaws are in a closed position, the elastic properties of the clip anchors the clip in place and allows for the grasper to be removed.

11. The clip of claim 10, wherein the primary sleeve has a close shape.

12. The clip of claim 10, wherein there is a cut opposite to atraumatic jaws for insertion of a tool to open and close the atraumatic jaws.

13. The clip of claim 10, wherein there are two holes in the front of the primary sleeve for the ends of tips of a tool to be inserted.

14. The clip of claim 13, wherein two small plates on the top and bottom of the jaws are located in front of each of the two holes in the primary sleeve to limit the insertion depth of a grasper's tips.

15. The clip of claim 14, wherein the two holes on the primary sleeve line up with the holes in or grooves on the track of the inner sleeve and with the protruding pins on the outer sleeve.

16. The clip of claim 10, wherein the primary sleeve is constructed with a semi-flexible material that allows for the sleeve to be expanded from a closed shape to an open shape.

17. The clip of claim 16, wherein the semi-flexible material has recoil properties that allow the sleeve to return to its closed shape after deformation to an open shape.

18. The clip of claim 10, wherein the primary sleeve includes two double walls.

19. The clip of claim 10, wherein the inner sleeve is located in-between the double walls of the primary sleeve.

20. The clip of claim 10, wherein the end of the inner sleeve is permanently attached to the bottom of the primary sleeve.

21. The clip of claim 10, wherein the outer sleeve fits over the primary sleeve.

22. The clip of claim 10, wherein two semi-flexible pins are affixed to the outer sleeve to align with the inner sleeve.

23. The clip of claim 10, wherein one end of the outer sleeve is permanently fixed to the primary sleeve.

24. The clip of claim 10, wherein the outer sleeve has elastic properties.

25. A clip comprising:
two flat plates,
a hinge at one end of the two flat plates,
pins for holding the gripping action of the clip; and
jaws having atraumatic grooved surfaces at the other end of the plates on the opposite side of the hinge for insertion of a grasper to open and close the jaws, such that when the jaws are in an open position, the clip is structured to receive the grasper and become an extension of the grasper, and when the jaws are in a closed position, the elastic properties of the clip anchors the clip in place and allows for the grasper to be removed.

26. The clip of claim 25, further comprising two closed shaped sleeves are attached to outside of top and bottom of the two flat plates and aligned so that tips of a tool pass through.

27. The clip of claim 25, further comprising small vertical plates, attached to the top and bottom of the outer surfaces of the two flat plates in front of sleeves limit the depth of penetration of a grasper during application.

28. The clip of claim 25, wherein the hinge provides elastic properties for the jaws of the clip.

* * * * *